US008955386B2

(12) United States Patent
Petschacher

(10) Patent No.: US 8,955,386 B2
(45) Date of Patent: Feb. 17, 2015

(54) SYSTEM FOR MEASURING THE LOAD ON A BRIDGE WHEN BEING USED BY A VEHICLE

(76) Inventor: Markus Petschacher, Feldkirchen (AT)

( * ) Notice: Subject to any disclaimer, the term of this patent is extended or adjusted under 35 U.S.C. 154(b) by 0 days.

(21) Appl. No.: 14/111,359

(22) PCT Filed: Apr. 10, 2012

(86) PCT No.: PCT/AT2012/000098
§ 371 (c)(1),
(2), (4) Date: Oct. 11, 2013

(87) PCT Pub. No.: WO2012/139145
PCT Pub. Date: Oct. 18, 2012

(65) Prior Publication Data
US 2014/0026671 A1 Jan. 30, 2014

(30) Foreign Application Priority Data

Apr. 11, 2011 (AT) .................................. A 513/2011

(51) Int. Cl.
G01M 5/00 (2006.01)
G01N 3/32 (2006.01)
(Continued)

(52) U.S. Cl.
CPC ................ *G01N 3/00* (2013.01); *G01G 19/024* (2013.01); *G01M 5/0008* (2013.01); *G01M 5/0041* (2013.01); *G01M 5/0066* (2013.01); *G01M 5/0083* (2013.01)
USPC .................................. 73/786; 73/788; 73/808

(58) Field of Classification Search
USPC ........... 73/786, 788, 794, 803, 808, 790, 795, 73/796
See application file for complete search history.

(56) References Cited

U.S. PATENT DOCUMENTS

| 4,901,575 A | 2/1990 | Bohannan et al. |
| 5,111,897 A | 5/1992 | Snyder et al. |
| 2004/0030507 A1* | 2/2004 | Jung ............................... 702/42 |

(Continued)

FOREIGN PATENT DOCUMENTS

| CA | 2564034 A1 | 4/2008 |
| DE | 102006053965 A1 | 7/2008 |

(Continued)

OTHER PUBLICATIONS

Ou et al.: "Development and performance of wireless sensor network for structural health monitoring", Proc. of SPIE. Smart Structures and Material, vol. 5391, Jul. 29, 2004, pp. 765-777, XP040183626.

(Continued)

*Primary Examiner* — Lisa Caputo
*Assistant Examiner* — Jonathan Dunlap
(74) *Attorney, Agent, or Firm* — Laurence A. Greenberg; Werner H. Stemer; Ralph E. Locher

(57) ABSTRACT

A system measures the load on a bridge when being used by a vehicle. The system has at least one measuring module with a plurality of measuring channel units which have associated separate sensors, preferably DMS sensors, which are intended to be fitted to the bridge. The sensors transmit measurement signals, preferably by wire, to the measuring channel units which are associated with each of the sensors and derive digital measurement data from the measurement signals. The measuring module also has an associated transmission interface in order to transmit the digital measurement data to a remote evaluation unit.

13 Claims, 5 Drawing Sheets

| (51) | Int. Cl. | |
|---|---|---|
| | *G01N 3/00* | (2006.01) |
| | *G01G 19/02* | (2006.01) |

(56) References Cited

U.S. PATENT DOCUMENTS

| 2005/0204825 A1 | 9/2005 | Kunerth et al. |
| 2006/0137914 A1 | 6/2006 | Hodac |
| 2007/0062289 A1 | 3/2007 | Heyman et al. |
| 2010/0238027 A1 | 9/2010 | Bastianini |

FOREIGN PATENT DOCUMENTS

| DE | 102008026483 A1 | 12/2009 |
| EP | 2192377 A1 | 6/2010 |
| JP | 2005030786 A | 2/2005 |
| JP | 2007120178 A | 5/2007 |
| SU | 809307 A1 | 2/1981 |
| WO | 2009063523 A2 | 5/2009 |

OTHER PUBLICATIONS

Yuri Tselishev et al., "Wireless Sensor Network Testbed for Structural Health Monitoring of Bridges", IEEE Sensors 2009, Oct. 1, 2009, pp. 1796-1799, XP055066927, DOI: 10.1109/ICSENS.2009.5398444, ISBN: 978-1-42-444548-6.

\* cited by examiner

150
SYSTEM FOR MEASURING THE LOAD ON A BRIDGE WHEN BEING USED BY A VEHICLE

BACKGROUND OF THE INVENTION

Field of the Invention

The invention relates to a system for measuring the load on a bridge when travelled by a vehicle.

It has for a long time been a concern to monitor bridge constructions with regards to their loading when they are travelled by vehicles, heavy lorries in particular, in order for example to ensure that maintenance operations or upkeep operations are carried out early, and as a result to prevent later complex repair operations and renovations.

It has already been suggested (cf. "Kleine Zeitung", 15 Apr. 2009, page 35), inter alia to use bridge monitoring with image recognition mechanisms, in order to detect the weight of lorries travelling over the bridge on the one hand and the axial loads on the other hand; the data obtained should be analysed with the aid of software. As passenger vehicles are also detected in the process, it was also regarded as advantageous in accordance with this suggestion that a complete traffic survey would be possible. As far as vehicles are concerned, speed and axial spacing in particular were detected in this case. The vehicles are detected via sensors and lorry classes are assigned to lorry classes inter alia on the basis of the number of axles and spacings.

Even if an improvement were achievable with this suggested system compared to earlier systems, there is yet a requirement as before for a measuring system which is of simple construction, reliable during operation and quickly supplies the desired data for the analysis with regards to a reliable bridge load analysis.

BRIEF SUMMARY OF THE INVENTION

To achieve the object set, the invention provides a system as stated in the independent claim. Advantageous embodiments and developments are defined in the dependent claims.

Thus, according to the invention, at least one measuring module is therefore provided on site, in the region of the bridge, this measuring module containing a plurality of measuring channel units, to which separate sensors, preferably strain gauge sensors (WSG—wire strain gauge) are connected. A measuring module of this type with the associated sensors therefore has a "spider"-type configuration of module and sensors, and generally a plurality of such measuring modules ("spiders") with associated sensors are attached on a bridge. The sensors can be arranged on the underside of the bridge, but theoretically also within the bridge structure, and they are used to measure the loading of the respective bridge in a suitable form, for example in the case of WSG sensors, by detecting flexure. Preferably, as mentioned, a plurality of such measuring modules are present and the measuring modules can also be combined in groups, depending on the local conditions. In order to detect the bridge girder system temperature and take the measured temperature into account during the evaluations of the loading data, it is expedient that the measuring module or at least one measuring module is connected to a temperature sensor. Also, with regards to the dynamic detection of the load measurement data, an acceleration sensor can be provided, which is connected to the or to at least one measuring module or is assigned to the same.

The measured data can then be transmitted via a router/computer and e.g. via the Internet to the central evaluation unit.

The measuring module or each measuring module is preferably accommodated in a housing, e.g. a metal housing, which is closed in a sealed manner, to protect the electronics.

Whilst the temperature sensor can for example be a digital temperature sensor, the loading sensors, particularly WSG sensors, are generally analogue sensors. In a corresponding embodiment, the sensors therefore output (at least in part) analogue measurement signals, and these analogue measurement signals are digitised in the measuring modules with the aid of an A/D converter provided there, in order to thus derive the digital measurement data for transmission to the remote analysis unit.

For each measuring module with associated sensors, provision is preferably made for the measurement signals of the sensors to be transmitted in a wired manner to the associated measuring module, to the associated measuring channel units, the wired transmission being readily possible, as only relatively short distances are provided for the transmission and the energy supply can also take place thereby and parallel thereto (power over Ethernet—PoE).

In the present measuring system, a plurality of decentralised measuring stations are therefore present, which are connected via a local network, a LAN (LAN—local area network). In this case, a local computer or server (here also termed slave computer) can be connected to the or to each measuring module, in order to prepare and temporarily store the data locally if necessary, before they are transmitted to the central evaluation unit, more precisely to an analysing computer. This transmission can in particular take place via a mobile Internet connection and a dedicated server or router, or a WLAN server, is accordingly provided, which is furthermore equipped with a GSM or UMTS modem.

Overall, a simple, readily scalable and in particular quickly and simply installable system is therefore provided. In this respect, it is also advantageous if the transmission interface is simultaneously set up for receiving a supply voltage for the measuring module, which has an associated energy supply unit. In this case, it is furthermore beneficial if the energy supply unit provides different voltages for digital or analogue switching parts of the measuring module.

The local server can control and monitor or manage the entire measuring system, that is to say the measuring modules with the sensors connected thereto, and prepare and also temporarily store the measurement data of all stations. In the case of an Internet connection for transmitting the measurement data, it is furthermore possible via the (WEB) server in the case of remote Internet-based remote access to operate all devices via a WEB browser and to configure the same for specific use situations from the central point.

In addition to the present measurement system with the measurement modules including sensors, it is also advantageous if a camera is attached on the bridge, in order to optically detect the vehicles travelling over the bridge from the side; two types of camera are provided during use, on the one hand overhead cameras, in order to obtain overview images of the vehicle, and on the other hand, high-speed cameras attached laterally to the street axis, in order to detect the vehicle axles here in particular and to couple the corresponding detections with the load measurement data, as are recorded by the strain gauge sensors, with regard to a simplified analysis.

A buffer memory for temporarily storing the transmitted measurement data can advantageously be connected upstream of the actual evaluation computer at the location of the central, remote evaluation unit.

Whilst, as mentioned, the signal transmission from the sensors to the respective measurement modem and also possibly from the measurement modem to the server or router preferably takes place in a wired manner in the region of the respective bridge, a wireless measurement data transmission from this local measurement arrangement to the remote evaluation unit is preferably provided.

As mentioned, the present measurement system enables low efforts for the installation on bridges to be monitored and nonetheless a centralised processing of the data and also monitoring of the systems. As a result, the overall operation process in the course of the measurements is simplified, and it is also made possible to carry out a plurality of measurements at various sites in parallel. Due to the decentralised measuring units, and the simple wiring, a clear cost advantage results and moreover, the present system can readily be adapted to specific measuring tasks, compared to systems currently available on the market. In this manner, the use of an efficient bridge measuring technology on a large scale is made possible with the present system. An advantageous use of the present measuring system consequently also results for toll systems and for traffic management.

The concept of the "distributed measuring station" is of particular significance for the present measuring system, i.e. the distribution of the measuring units in measuring modules with a limited number of connected sensors in each case, for example as has proven particularly beneficial in practice, with up to eight (WSG) sensors per measuring module, these measuring modules then delivering the corresponding measurement data of the associated sensors in digital form. These distributed measuring "stations" can be synchronised in time by the respective local server, i.e. the local server keeps the associated measuring modules or measuring stations in synchronicity.

BRIEF DESCRIPTION OF THE SEVERAL VIEWS OF THE DRAWING

The invention will hereinafter be explained still in more detail on the basis of particularly preferred exemplary embodiments illustrated in the drawing, to which it should not be restricted however. In detail, in the drawing.

DESCRIPTION OF THE INVENTION

Figure 1:
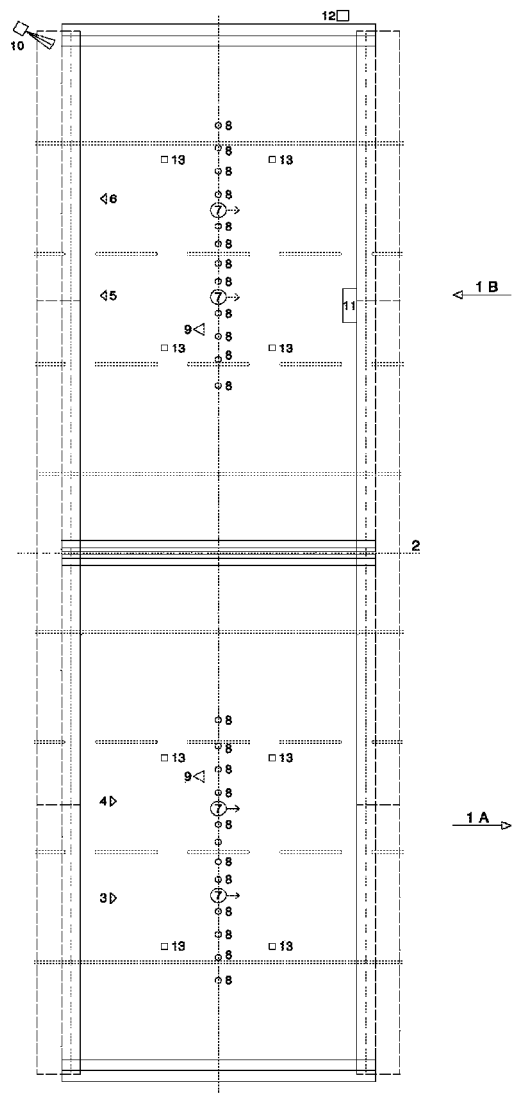
FIG. 1 shows a completely schematic illustration of a part of a motorway bridge with positions for measuring modules and sensors of the present measuring system indicated therein.

A part of a bridge 1, for example of a motorway bridge with two directions of travel 1A, 1B, is shown quite schematically in FIG. 1, lanes 3, 4 and 5, 6 respectively being present on both sides of the axis 2 of the motorway bridge 1. On the underside of the bridge 1, on the one hand measuring modules 7 at the positions indicated in FIG. 1 and on the other hand positions of sensors 8, particularly WSG sensors and also a temperature sensor 9 can be seen; the positions of the WSG sensors 8 are indicated by small rings, but for the sake of simplicity, they are not further designated with designated reference numbers. It can be seen from the illustration in FIG. 1 however that on the left side according to the illustration, eight sensors 8 are connected to the measuring module 7, whereas if necessary fewer than eight WSG sensors 8 can also be provided.

Additionally, a video camera 10 can also be seen from FIG. 1, which is provided to detect vehicles travelling over the bridge 1, particularly lorries and in particular the number of axles thereof. Further, a power supply box 11 for the local network (LAN) with the measuring modules and also a local router 12 are shown schematically.

The individual components of the system, namely measuring modules 7 with sensors 8, 9, but also with the router 12 and camera 10, are explained in more detail hereinafter with reference to FIGS. 2 to 5.

ADMP units 13 (ADMP—axle detection measurement point) are also furthermore illustrated in FIG. 1 with small squares. Here, these are sensors with the aid of which the speed of the vehicles can be determined.

Figure 2A:
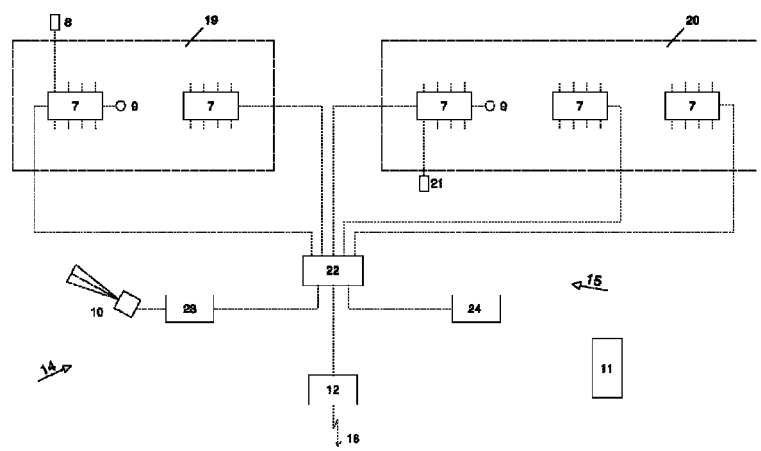
FIG. 2 schematically shows the structure of the present system for measuring the loading of bridges in the part figures FIG. 2A (local part of the measuring system) and FIG. 2B (remote central part of the system)

The upper part of FIG. 2, the part FIG. 2A, shows a local arrangement 14 of the present measuring system by way of example, which (as a LAN network 15) is connected to a central, remote evaluation region 17 with an evaluation unit 18 of the system via an Internet connection 16 which is only illustrated schematically. It should of course be the case that a plurality of such local measuring arrangements 14 cooperate with the central region 17, as is shown in FIG. 2, even if only a single local measuring arrangement 14 is shown in FIG. 2.

According to FIG. 2A, the local arrangement 14 comprises two groups 19, 20 for example, with a plurality of measuring modules 7 in each case, which have corresponding measuring channel units with connection points for sensors, namely load sensors 8 in the form of WSG sensors, temperature sensors 9, but if necessary also acceleration sensors 21. The measuring modules 7 according to FIG. 1 will be explained in more detail hereinafter on the basis of FIG. 3 and their measuring channel units will be explained on the basis of FIGS. 4 and 5.

The individual measuring modules 7, which are for example arranged in an Ethernet network 15, are connected to a PoE switching module 22 (PoE—Power over Ethernet) according to FIG. 2. The server/router 12 already mentioned on the basis of FIG. 1 is then connected to this switching module 22, which acts as router, as WLAN server and also as GSM or UMTS modem for the Internet connection 16, for network administration, for data preprocessing and for buffer storage.

Furthermore, the camera 10 is shown in FIG. 2A, which is connected via a data grabber 23, that is to say a data reader, to the PoE switching module 22. Moreover, as shown in the example according to FIG. 2A, a slave computer 24 can be provided for precalculations in the course of the data analysis, this slave computer 24 also being connected to the switching module 22.

Figure 2B:
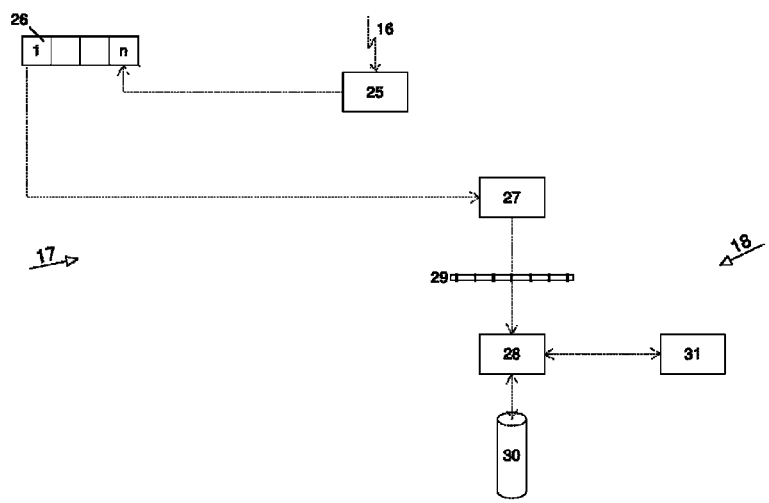

An upload server 25 is provided in the central measuring system region 17, via which the Internet connection 16 is realised. A buffer memory 26, a type of wait queue, is connected to this upload server 25, from which the measurement data make it via a transmitter 27 to the actual central evaluation unit 18 with a central evaluation computer 28—via a firewall 29. The central computer 28 accesses a database 30 and it operates on the basis of analysis software which is represented in FIG. 2B with an analysis module 31.

The division of the measuring modules 7, etc. into groups, e.g. 19, 20 is advantageous if a grouping into logical units appears expedient from a statically constructive viewpoint. In this case, handling the measurement data in groups may entail a significantly simpler signal processing.

The measuring modules 7 are an important part of the present measuring system insofar as they entail a great proximity to the actual sensors 8, 9, but also 21, so that analogue sensor signals can already be digitised after a short distance. As will be explained in more detail on the basis of FIG. 3, in the preferred embodiment, up to eight sensors, particularly WSG sensors 8 are kept synchronous with a module 7 of this type.

All measuring modules 7 are supplied with electrical energy in the exemplary embodiment shown by means of the PoE module 22. In this case, it is advantageous that thin cables can be used, which can be laid easily. A limitation is imposed by a maximum length of 100 m.

All data are sent on-line via the server or router 12, and it is preferably used at the same time as a central computer for the local part 14, whereby it synchronises the measuring modules 7 in the individual groups 19, 20; the router 12 permanently receives data packets, organises the same and forms so-called dac files for each group, in which one measurement result or a plurality of measurement results can be contained.

The acceleration sensor 21 is not absolutely necessary for the present measuring system, it can however be integrated in the measuring system if required, specifically either as an analogue sensor at one of the outputs for the WSG sensors 8, as shown in FIG. 2A, or as a digital sensor, particularly at an RS485 interface (cf. also FIGS. 3 and 5 below).

The local slave server 24 can additionally be used to receive data and carry out on-site calculations parallel to the router or server 12.

The wait queue 26 in the central region 17 is not only used as an asynchronous memory, but also offers the possibility of carrying out maintenance and installation operations on the central computer 28. The transmitter 27 is a temporally triggered service which reads the wait queue 26 with an upper limit of packets and passes the same through the firewall 29 to the computer 28. The camera 10 is a high-speed camera which can be seen as an additional "sensor"; for determining the geometric dimensions of a vehicle travelling over the bridge 1 (FIG. 1), this camera 10 should generate at least 200 fps (frames per second). The analysis then takes place in a time-delayed manner with the aid of the SW module 31. The data grabber 23 is strictly speaking a computer with Gigabit Ethernet (GigE), in order to ensure communication with the camera 10. The reader software and the server/router 12 are expediently synchronised with one another.

The database 30 centrally contains all relevant data of each measurement project with respect to the respective bridge 1. This database 30 can however of course also manage a plurality of measurements running at the same time.

Figure 3:
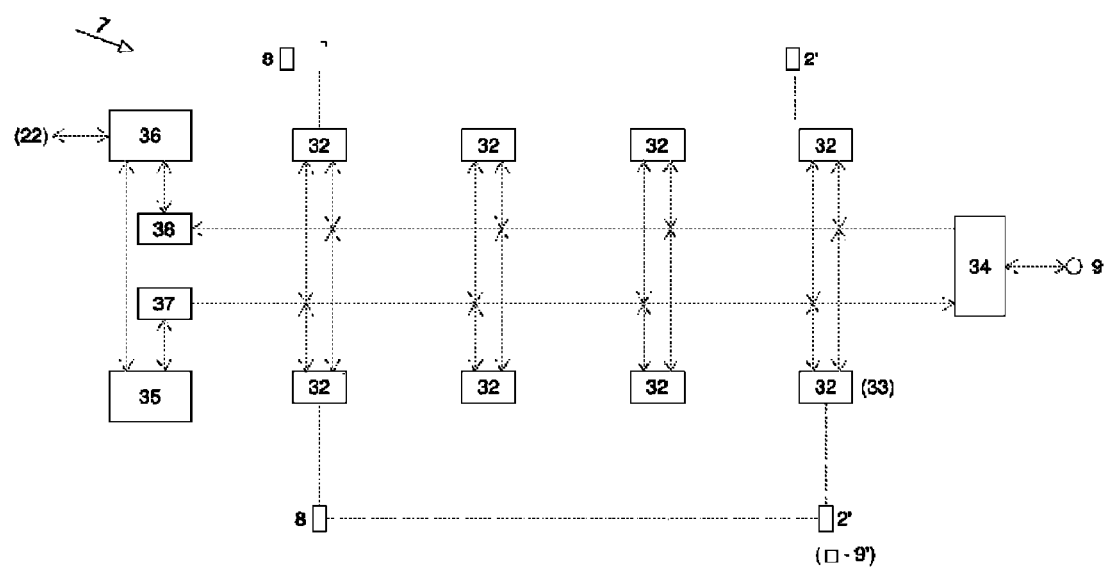
FIG. 3 shows a block diagram of a measuring module provided in the system according to FIG. 2A, and FIGS. 4 and 5 show exemplary embodiments for two different measuring channel units, namely for a WSG sensor (FIG. 4) and for a temperature sensor (FIG. 5).

A block diagram of a measuring module 7 is shown in more detail in FIG. 3, individual sensors connected to this measuring module also being indicated. The measuring module 7 for example detects the analogue signals of up to eight WSG sensors 8, which are mounted on the bridge 1 to be measured (FIG. 1) and converts the analogue signals into individual measuring channel units 32 or 33. As already mentioned, it is advantageous to record the temperature of the supporting structure in the group 19 or 20 (FIG. 2A), so that global strain changes of the supporting structure of the bridge 1 can be taken into consideration. This temperature sensor can for example be provided as a digital sensor 9 which can be connected to an RS485 interface 34 of the measuring module 7. Alternatively, in the case of an analogue temperature sensor 9', a suitable measuring channel unit 33 with A/D converter can be assigned, cf. also FIG. 5 which will be explained in more detail hereinafter.

Above all, the strain gauge sensors 8 are important, which as analogue displacement transducers are used to measure strains on the underside of the bridge 1 as a consequence of loading during the travelling of heavy vehicles, in particular over the bridge.

The voltage supply of the measuring module 7, in which all components are preferably accommodated on a common circuit board, preferably takes place, as mentioned, via Ethernet—PoE, each measuring module 7 having a corresponding PoE module 35 connected to an interface module 36, e.g. a "linux embedded module". A supply voltage stage 37 is then connected to the PoE module 35, which in the example shown provides two operating voltages, namely 3.3 V for all digital components of the measuring module 7 and 5 V for all analogue components. A different supply voltage, e.g. 2.5 V would theoretically also be possible for the analogue components however.

The PoE module 35 for example contains a DC/DC converter with buck topology in a per se conventional manner, which steps down the 48 V of the PoE supply voltage to 6 V. Subsequently, a second DC/DC buck converter is provided, which regulates this voltage from 6 V to 3.3. V for supplying the digital components, particularly also the linux module 36. A third, linear converter converts the 6 V supply voltage to a 5 V voltage for the analogue technology; a linear converter is therefore preferably chosen here, as the accuracy or cleanness of the voltage is then ensured.

As already mentioned previously, a corresponding unit (11 in FIG. 1) can be provided on the bridge 1 for power supply. This power supply 11 can be realised with 4×12 V batteries, in order to ensure the 48 V voltage possible for the PoE technology. Instead of the 4×12 V batteries, e.g. car batteries, fewer batteries, at least with 36 V output voltage, can also be provided, an electronic voltage increase (so-called boost converter) then needing to be provided, as is known per se. The separate voltage supply for the analogue and digital parts in the measuring module 7 has the advantage that interferences due to cross-coupling can be prevented, and the size of the analogue voltage can also be optimally adapted to the requirements of the measuring technology in the process.

The Linux Embedded Module 36 is used for communicating between the measuring module 7 and the local network 15, the Ethernet; for example a module 36 with Linux operating system is used, the module 36 in this case having a 10/100 megabit Ethernet connection and also providing serial interfaces (asynchronous, SPI—Serial Peripheral Interface, etc.). Due to the limited connections, the SPI interface for the individual measuring channel units 32 etc. is produced via an extended SPI interface 38.

Figure 4:
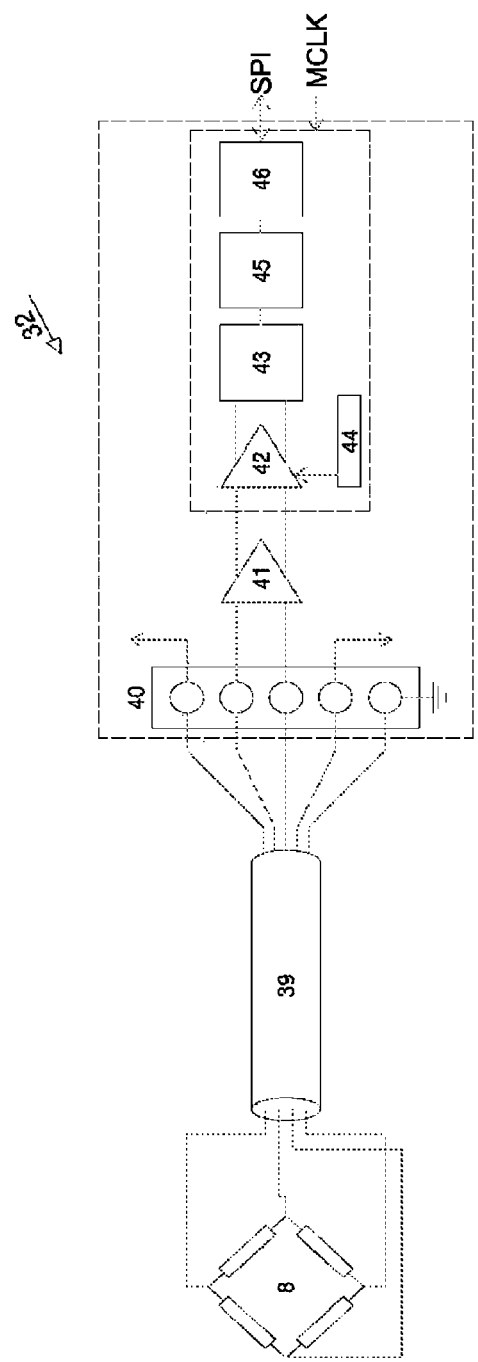
Figure 5:
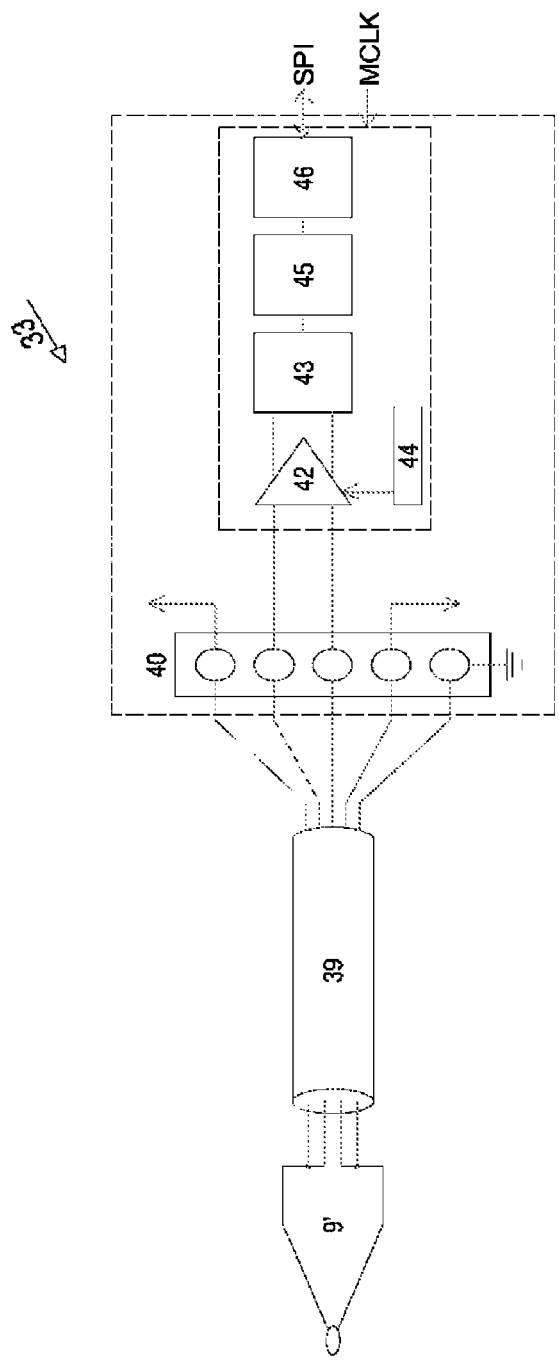

The measuring module 7 combines a highly precise measuring technology with fast digital signal processing, as also results in more detail from the following description of FIGS. 4 and 5. In this case, an optimisation is possible with regard to the prevention of faults of the measuring technology, for example by means of coupling effects, crosstalk, etc.

Preferably, the installation of the measuring module 7 takes place into a closed housing, particularly a metal housing, preferably a screwed aluminium housing, which can have dimensions of 220 mm×123 mm×80 mm for example. The measuring module 7 is in this case suitable for operation at an ambient temperature of −40° C. to +50° C.

Shown in FIG. 4 by way of example is a measuring channel 32 connected to a WSG sensor 8 via a coaxial cable 39, the measuring channel unit 32 being a component of the measuring module 7, as mentioned, on which the for example up to 8 or 9 different sensors can be attached similarly to a "spider" via lines (coaxial cable 39). Each measuring channel 32 provides soldering terminals 40 on the circuit board for connecting the shielded 4-pole coaxial cable 39 to the associated sensor 8 (wire strain gauges in a bridge circuit). A fifth soldering point is connected to earth or to the shielding of the coaxial cable 39. Two soldering points are used for optional voltage supply (3.3 V or 5 V as explained above), and two soldering points or signal connections are connected to a pre-amplifier 41 in the measuring channel 32, which for example provides amplification of up to 1400 times, an amplification of 300 times in the example tested. From this pre-amplifier 41, the measurement signals (differential bridge signals) make it via a programmable amplifier 42 (PGA—programmable gain amplifier) to an A/D converter 43. At the amplifier 42, the amplification can be set via an input unit 44, e.g. to a ×1, ×2, ×4, ×8, ×16, ×32, ×64 amplification.

The A/D converter 43 is for example a 16 bit sigma-delta A/D converter. From the point of view of the respective measuring module 7, an exact synchronisation of the sampling times of the A/D converter 43 of the eight measuring channels is not required, as the measurement signals can be analysed integrally. Comprehensive setting options for the calibration and execution of the A/D conversion result from the pre-amplification 41, 42 and also the converter 43.

A filter 45 is then illustrated symbolically in FIG. 4. However, it is to be added to this that a hardware filter is preferably not used in the context of the present measuring system, but a software filter is rather executed, to the extent that this is necessary.

Finally, an SPI interface 46 can also be seen from FIG. 4, which produces the connection to the Ethernet or to the module 22 (FIG. 2A) via the SPI interface 38 and the embedded module 36.

The thus-described measuring electronics deliver digital measured values, which correspond to a determined bridge voltage depending on the setting of the amplification at the amplifier 43. The electrical amplification of the system can be defined thus. The zero point of the system can be different from the zero value due to offsets in the sensor or in the measuring circuit or else underlie any drifts, e.g. with temperature. The A/D converter 43 therefore offers an option for calibration, so that precise, reproducible measured values can be obtained over the entire temperature range occurring in practice.

As mentioned, digital temperature sensors 9 or else analogue temperature sensors 9', for example Pt100 sensors, can be used for temperature measurement. An example for a measuring channel 33 with an analogue temperature sensor 9' of this type is shown in FIG. 5, the structure of this measuring channel 33 corresponding in principle to a large extent to that of the measuring channel 32 of FIG. 4, so that for corresponding components, the same reference numbers are used and a new description of this measuring channel unit, which concerns the structure, can be dispensed with. A similar structure of the measuring channel incidentally exists in the case of an (analogue) acceleration sensor 21 (FIG. 2A).

The temperature measurement should be carried out with sensors 9 or 9' of such a type that a resolution of 0.1° C. and an accuracy of +/−1° C. is achieved.

A difference in the configuration of FIG. 5 compared to that of FIG. 4 consists in the fact that in the case of a temperature sensor 9', a pre-amplifier 41 is not required. A stable measurement with the required resolution is hereby possible. The achievement of the desired accuracy can however also be dependent on the scattering of the resistance values of the Pt100 sensors 9', which can be taken into account with a corresponding calibration.

A temperature measurement is in each case only required for an entire measurement cycle, so that the measurement of the temperature can take place at comparatively large time intervals, e.g. in intervals of one second or more. The time schedule of the temperature measurement can be set via the software. The analogue signal received from the sensor 9' is in turn digitised in the measuring channel 33 (cf. AD converter 43) and is subsequently converted into the actual temperature value by means of corresponding formulae in the embedded module 36 (cf. FIG. 3).

Preferably, however, as mentioned previously, digital temperature sensors are used (cf. FIG. 3), highly precise digital semiconductor temperature sensors 9 having meanwhile become available, which output the temperature value directly in digital form, for example via I2C or SPI interfaces. Digital temperature sensors 9' of this type also enable larger distances to the measuring modules 7 or the RS485 interfaces 34 thereof (cf. FIG. 3).

As far as the invention has previously been explained on the basis of particularly preferred exemplary embodiments, further amendments and modifications are of course possible in the context of the invention. Thus, it is for example conceivable in the case of small bridge constructions to only provide one measuring module 7 with a corresponding number of measuring channels 32/33, e.g. also only six, although the invention produces its particular advantages if a plurality of measuring modules 7 of this type is provided on a bridge 1, specifically in the corresponding grouping, as explained. The advantages of a simple mounting, an exact and fast measured value determination and also a fast and precise analysis of the measured data are enabled by means of the described distributed system, cf. in particular FIG. 2 with the Part FIGS. 2A and 2B.

The invention claimed is:

1. A system for measuring a load on a bridge when being traversed by a vehicle, the system comprising:
 a plurality of measuring modules each having a plurality of measuring channel units with A/D converters;
 a plurality of separate strain gauge sensors associated with said measuring modules, and provided for attaching on the bridge, said strain gauge sensors transmitting analog measurement signals in a wired manner to said measuring channel units assigned to them in each case, said measuring channel units deriving digital measurement data from the analog measurement signals by means of said A/D converters;
 a POE switching module;
 a local server/router;
 a remote evaluation unit, the digital measurement data being transmitted from said local server/router via a radio data transmission to said remote evaluation unit; and
 said measuring modules each having a respective transmission interface and connected in parallel and in a wired manner to said PoE switching module and via said PoE switching module to said local server/router, as a result of which a local network (LAN) is formed, in that said local server/router keeping said measuring modules in synchronicity.

2. The system according to claim 1, wherein said measuring modules each have an energy supply unit and said respective transmission interface is simultaneously set up for receiving a supply voltage for a respective one of said measuring modules, which has said energy supply unit.

3. The system according to claim 2, wherein said energy supply unit provides different voltages for digital and analog switching parts of a respective one of said measuring modules.

4. The system according to claim 1, wherein individual ones of said measuring modules are combined into groups.

5. The system according to claim 1, further comprising a temperature sensor detecting a temperature of a bridge supporting structure, at least one of said measuring modules is connected to said temperature sensor.

6. The system according to claim 1, further comprising an acceleration sensor connected to at least one of said measuring modules.

7. The system according to claim 1, further comprising housings and each of said measuring modules is disposed in one of said housings being closed in a sealed manner.

8. The system according to claim 7, wherein said housings are made of metal.

9. The system according to claim 1, further comprising a local computing device connected to each of said measuring modules for carrying out on-site calculations.

10. The system according to claim 1, wherein said local server/router is a wireless local area network (WLAN) server.

11. The system according to claim 1, wherein said local server/router has a modem for data transmission selected from the group consisting of a global system for mobile communications modem and a universal mobile telecommunications system modem.

12. The system according to claim 1, further comprising a camera for lateral vehicle detection, including for detecting vehicle axles, and adapted for attachment on the bridge.

13. The system according to claim 1, further comprising a buffer memory coupled to said remote evaluation unit.

* * * * *